(12) United States Patent
Arista et al.

(10) Patent No.: US 7,807,698 B2
(45) Date of Patent: Oct. 5, 2010

(54) AZABICYCLO[3.1.0]HEXANE DERIVATIVES AS MODULATORS OF THE DOPAMINE D3 RECEPTOR

(75) Inventors: Luca Arista, Verona (IT); Giorgio Bonanomi, Verona (IT); Dieter Hamprecht, Verona (IT); Fabrizio Micheli, Verona (IT)

(73) Assignee: Glaxo Group Limited, Middlesex (GB)

( * ) Notice: Subject to any disclaimer, the term of this patent is extended or adjusted under 35 U.S.C. 154(b) by 97 days.

(21) Appl. No.: 11/917,355

(22) PCT Filed: Jun. 13, 2006

(86) PCT No.: PCT/EP2006/005767
§ 371 (c)(1),
(2), (4) Date: Dec. 13, 2007

(87) PCT Pub. No.: WO2006/133945
PCT Pub. Date: Dec. 21, 2006

(65) Prior Publication Data
US 2008/0227837 A1    Sep. 18, 2008

(30) Foreign Application Priority Data
Jun. 14, 2005 (GB) ................... 0512099.3
Mar. 10, 2006 (GB) ................... 0604897.9

(51) Int. Cl.
*A61K 31/41* (2006.01)
*C07D 257/00* (2006.01)
*C07D 249/08* (2006.01)

(52) U.S. Cl. ............ 514/341; 546/272.4; 548/152; 548/263.2

(58) Field of Classification Search ............... 514/341; 546/272.4; 548/152, 263.2
See application file for complete search history.

(56) References Cited

U.S. PATENT DOCUMENTS

| | | | |
|---|---|---|---|
| 2007/0142438 A1 * | 6/2007 | Arista et al. ............... | 514/341 |
| 2007/0249642 A1 | 10/2007 | Bertani et al. ............... | 514/269 |
| 2008/0058398 A1 | 3/2008 | Anderton et al. ............. | 514/374 |
| 2008/0167357 A1 | 7/2008 | Hamprecht et al. ........ | 514/384 |
| 2008/0176917 A1 * | 7/2008 | Andreotti et al. ............. | 514/384 |
| 2008/0227837 A1 * | 9/2008 | Arista et al. ................ | 514/384 |
| 2008/0242715 A1 * | 10/2008 | Capelli et al. ............... | 514/384 |
| 2009/0030062 A1 | 1/2009 | Gentile et al. ............... | 514/412 |
| 2009/0036461 A1 | 2/2009 | Hamprecht et al. ..... | 514/252.06 |
| 2009/0124629 A1 | 5/2009 | Bonanomi et al. ...... | 514/252.06 |
| 2009/0221593 A1 * | 9/2009 | Bonanomi et al. ........... | 514/249 |
| 2009/0221618 A1 | 9/2009 | Arista et al. ................ | 514/274 |

FOREIGN PATENT DOCUMENTS

| | | | |
|---|---|---|---|
| WO | WO 00/42037 A | | 7/2000 |
| WO | WO 01/98267 A | | 12/2001 |
| WO | WO/2005/080382 | * | 1/2005 |
| WO | WO 2005/080382 A | | 9/2005 |

OTHER PUBLICATIONS

Patini et al, Chem. Rev., 1996, 96(8), pp. 3147-3176, esp. p. 3150.*
U.S. Appl. No. 11/917,352, filed Jun. 13, 2006, Arista, et al.
U.S. Appl. No. 12/295,024, filed Mar. 30, 2007, Bertani, et al.
U.S. Appl. No. 12/295,304, filed Mar. 30, 2007, Bertani, et al.

* cited by examiner

*Primary Examiner*—Susannah Chung
(74) *Attorney, Agent, or Firm*—James M. Kanagy; Edward R. Gimmi; Charles M. Kinzig

(57) ABSTRACT

The present invention relates to novel compounds of formula (I) or a pharmaceutically acceptable salt thereof:

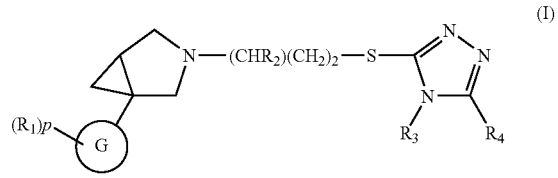

wherein
G is selected from a group consisting of: phenyl, pyridyl, benzothiazolyl, indazolyl;
p is an integer ranging from 0 to 5;
$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$; or corresponds to a group $R_5$;
$R_2$ is hydrogen or $C_{1-4}$alkyl;
$R_3$ is $C_{1-4}$alkyl;
$R_4$ is $C_{1-4}$ alkyl or $C_{1-6}$ cycloalkyl optionally substituted by 1 or 2 substituents selected from the group consisting of: halogen, cyano, $C_{1-4}$alkyl, halo$C_{1-4}$alkyl, $C_{1-4}$alkoxy, $C_{1-4}$alkanoyl;
$R_5$ is a moiety selected from the group consisting of: isoxazolyl, —$CH_2$—N-pyrrolyl, 1,1-dioxido-2-isothiazolidinyl, thienyl, thiazolyl, pyridyl, 2-pyrrolidinonyl, and such a group is optionally substituted by one or two substituents selected from: halogen, cyano, $C_{1-4}$alkyl, halo$C_{1-4}$alkyl, $C_{1-4}$alkoxy, $C_{1-4}$alkanoyl;

processes for their preparation, intermediates used in these processes, pharmaceutical compositions containing them and their use in therapy, as modulators of dopamine $D_3$ receptors, as antipsychotic agents, or to treat obsessive compulsive spectrum disorders or premature ejaculation.

5 Claims, No Drawings

AZABICYCLO[3.1.0]HEXANE DERIVATIVES AS MODULATORS OF THE DOPAMINE D3 RECEPTOR

This application is a 35 U.S.C. 371 application of International Application No. PCT/EP2006/005767, filed 13 Jun. 2006, and which claims the benefit of Provisional Application No. GB0604897.9, filed 14 Jun. 2005.

The present invention relates to novel compounds, processes for their preparation, intermediates used in these processes, pharmaceutical compositions containing them and their use in therapy, as modulators of dopamine $D_3$ receptors.

Recently a patent application has been published as WO2005/080382 and discloses the following compounds of formula (I) or a salt thereof:

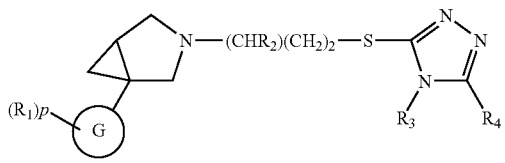

wherein
G is selected from a group consisting of: phenyl, pyridyl, benzothiazolyl, indazolyl;
p is an integer ranging from 0 to 5;
$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl; or corresponds to a group $R_5$;
$R_2$ is hydrogen or $C_{1-4}$alkyl;
$R_3$ is $C_{1-4}$alkyl;
$R_4$ is hydrogen, or a phenyl group, a heterocyclyl group, a 5- or 6-membered heteroaromatic group, or a 8- to 11-membered bicyclic group, any of which groups is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl;
$R_5$ is a moiety selected from the group consisting of: isoxazolyl, —$CH_2$—N-pyrrolyl, 1,1-dioxido-2-isothiazolidinyl, thienyl, thiazolyl, pyridyl, 2-pyrrolidinonyl, and such a group is optionally substituted by one or two substituents selected from: halogen, cyano, $C_{1-4}$alkyl, halo$C_{1-4}$alkyl, $C_{1-4}$alkoxy, $C_{1-4}$alkanoyl;

and when $R_1$ is chlorine and p is 1, such $R_1$ is not present in the ortho position with respect to the linking bond to the rest of the molecule; and when $R_1$ corresponds to $R_5$, p is 1.

None of the above references disclosed compounds falling into the scope of the present invention.

A new class of compounds which have affinity for dopamine receptors, in particular the dopamine $D_3$ receptor has been found. These compounds have potential in the treatment of conditions wherein modulation of the $D_3$ receptor is beneficial.

The present invention provides a compound of formula (I) or a pharmaceutically acceptable salt thereof:

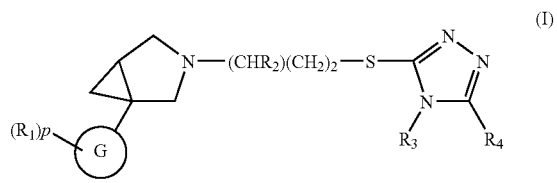

wherein
G is selected from a group consisting of: phenyl, pyridyl, benzothiazolyl, indazolyl;
p is an integer ranging from 0 to 5;
$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$; or corresponds to a group $R_5$;
$R_2$ is hydrogen or $C_{1-4}$alkyl;
$R_3$ is $C_{1-4}$alkyl;
$R_4$ is hydrogen, $C_{1-4}$ alkyl or $C_{1-6}$ cycloalkyl optionally substituted by 1 or 2 substituents selected from the group consisting of: halogen, cyano, $C_{1-4}$alkyl, halo$C_{1-4}$alkyl, $C_{1-4}$alkoxy, $C_{1-4}$alkanoyl;
$R_5$ is a moiety selected from the group consisting of: isoxazolyl, —$CH_2$—N-pyrrolyl, 1,1-dioxido-2-isothiazolidinyl, thienyl, thiazolyl, pyridyl, 2-pyrrolidinonyl, and such a group is optionally substituted by one or two substituents selected from: halogen, cyano, $C_{1-4}$alkyl, halo$C_{1-4}$alkyl, $C_{1-4}$alkoxy, $C_{1-4}$alkanoyl.

Because of the presence of the fused cyclopropane compounds of formula (I) are believed to have a "cis" disposition of the substituents (both groups linked to the bicyclic ring system are on the same face of this bicyclic ring system).

In another embodiment of the present invention compounds of formula (I)' are provided which correspond to the compounds of formula (I) having "cis" disposition, represented by the bold highlight of the bonds

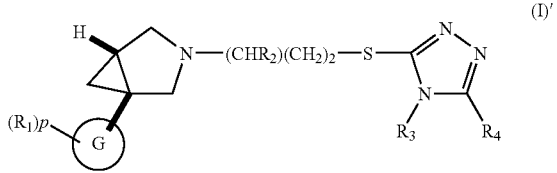

wherein G, p, $R_1$, $R_2$, $R_3$, $R_4$, and $R_5$ are defined as above for compounds of formula (I).

It will be appreciated that compounds of formula (I)' possess at least two chiral centres, namely at position 1 and 5 in the 3-azabicyclo[3.1.0]hexane portion of the molecule. Because of the fixed cis disposition, the compounds may exist in two stereoisomers which are enantiomers with respect to the chiral centres in the cyclopropane. It will also be appreciated, in common with most biologically active molecules that the level of biological activity may vary between the individual stereoisomers of a given molecule. It is intended that the scope of the invention includes all individual stereoisomers (diastereoisomers and enantiomers) and all mixtures thereof, including but not limited to racemic mixtures, which demonstrate appropriate biological activity with reference to the procedures described herein.

In compounds of formula (I)' there are at least two chiral centres, which are located in the cyclopropane portion, as depicted below (the bold highlight of the bonds means the "cis" configuration):

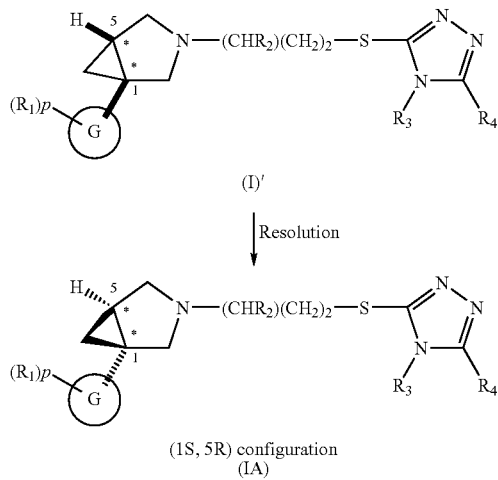

(I)'

↓ Resolution (1S, 5R) configuration
(IA)

when G is one of the heteroaromatic group described the configuration may become (1R,5R)
due to different Cahn-Ingold-Prelog nomenclature priorities In a further embodiment of the present invention compounds of formula (IA) are provided that correspond to stereochemical isomers of compounds of formula (I)', enriched in configuration (1S,5R) (or possibly (1R,5R) when G is one of the heteroaromatic group described)

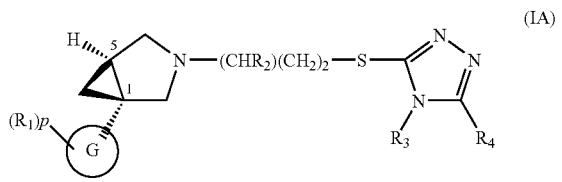

(IA)

wherein G, p, $R_1$, $R_2$, $R_3$, $R_4$, and $R_5$ are defined as above for compounds of formula (I)' or a pharmaceutically acceptable salt thereof.

It is intended in the context of the present invention that stereochemical isomers enriched in configuration (1S,5R) (or possibly (1R,5R) when G is one of the heteroaromatic group described) of formula (IA) correspond in one embodiment to at least 90% e.e. In another embodiment the isomers correspond to at least 95% e.e. In another embodiment the isomers correspond to at least 99% e.e.

In another embodiment of the present invention the stereochemical isomers enriched in configuration (1R,5S) are provided.

The term "$C_{1-4}$alkyl" refers to an alkyl group having from one to four carbon atoms, in all isomeric forms, such as methyl, ethyl, propyl, isopropyl, butyl, isobutyl, sec-butyl and tert-butyl. The term "n-$C_{1-4}$alkyl" refers to the unbranched alkyls as defined above.

The term '$C_{1-4}$ alkanoyl group' as used herein may be a linear or a branched chain alkanoyl group, for example acetyl, ethylcarbonyl, n-propylcarbonyl, i-propyl carbonyl, n-butyl-carbonyl or t-butylcarbonyl and the like.

The term 'halo $C_{1-4}$ alkyl' as used herein means an alkyl group having one or more carbon atoms and wherein at least one hydrogen atom is replaced with halogen such as for example a trifluoromethyl group and the like.

The term 'halo $C_{1-4}$ alkoxy group' as used herein may be a $C_{1-4}$ alkoxy group as defined before substituted with at least one halogen, preferably fluorine, such as $OCHF_2$, or $OCF_3$.

The term "$SF_5$" refers to pentafluorosulfanyl.

The term "$C_{1-6}$cycloalkyl" refers to a cicloalkyl group having from one to six carbon atoms.

The term "$C_{1-4}$alkoxy" refers to a straight chain or branched chain alkoxy (or "alkyloxy") group having from one to four carbon atoms, such as methoxy, ethoxy, propoxy, isopropoxy, butoxy, isobutoxy, sec-butoxy and tert-butoxy.

The term "halogen" and its abbreviation "halo" refer to fluorine (F), chlorine (Cl), bromine (Br) or iodine (I). Where the term "halo" is used before another group, it indicates that the group is substituted by one, two or three halogen atoms. For example, "halo$C_{1-4}$alkyl" refers to groups such as trifluoromethyl, bromoethyl, trifluoropropyl, and other groups derived from $C_{1-4}$alkyl groups as defined above; and the term "halo$C_{1-4}$alkoxy" refers to groups such as trifluoromethoxy, bromoethoxy, trifluoropropoxy, and other groups derived from $C_{1-4}$alkoxy groups as defined above.

Any of these groups may be attached to the rest of the molecule at any suitable position.

As used herein, the term "salt" refers to any salt of a compound according to the present invention prepared from an inorganic or organic acid or base, quaternary ammonium salts and internally formed salts. Physiologically acceptable salts are particularly suitable for medical applications because of their greater aqueous solubility relative to the parent compounds. Such salts must clearly have a physiologically acceptable anion or cation. Suitably physiologically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-physiologically acceptable anion or cation are within the scope of the invention as useful intermediates for the preparation of physiologically acceptable salts and/or for use in non-therapeutic, for example, in vitro, situations.

In one embodiment, $R_1$ is halogen, cyano, acetyl, trifluoromethyl, trifluoromethoxy.

In one embodiment, $R_2$ is hydrogen. In another embodiment $R_2$ is $C_{1-4}$ alkyl (e.g. methyl).

In one embodiment, $R_5$ is a group selected from: isoxazolyl, 2-pyrrolidinonyl, 1,1-dioxido-2-isothiazolidinyl which is optionally substituted by one or two substituents selected from: halogen, cyano, $C_{1-2}$alkyl (e.g. methyl), halo$C_{1-2}$alkyl (e.g. trifluoromethyl), $C_{1-2}$alkoxy (e.g. methoxy), $C_{1-3}$alkanoyl (e.g. acetyl).

Suitably, $R_1$ is bromo, fluoro, trifluoromethoxy, cyano, hydroxy, chloro, methoxy, tert-butyl, trifluoromethyl.

Suitably, $R_1$ is trifluoromethyl.

Suitably, $R_5$ is isoxazolyl, 2-pyrrolidinonyl, —$CH_2$—N-pyrrolyl, 1,1-dioxido-2-isothiazolidinyl, 2-thienyl, 2-pyridyl, 2-thiazolyl.

In one embodiment, p is 1 or 2.

In another embodiment p is 0.

In one embodiment, $R_4$ may be an optionally substituted linear or branched alkyl (e.g. methyl or t-butyl), or an optionally substituted cycloalkyl (e.g. cyclopropyl or cyclopentyl).

In another embodiment, $R_4$ may be methyl, t-butyl, cyclopropyl, cyclopentyl.

In a further embodiment, $R_4$ is hydrogen.

In one embodiment, $R_3$ is methyl.

In one embodiment, a compound of formula (IB) or a salt thereof is provided, wherein $R_1$, p, $R_3$ and $R_4$ are as defined for formula (I):

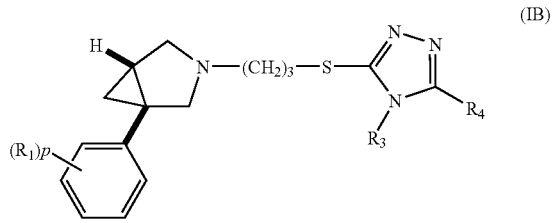

(IB)

In Formula (IB), in one embodiment, $R_3$ is methyl, $R_1$ is trifluoromethyl, p is 1 and $R_4$ may be an optionally substituted linear or branched alkyl, or an optionally substituted cycloalkyl.

Examples of $R_4$ include methyl, t-butyl, cyclopropyl, cyclopentyl.

In Formula (IB), in another embodiment, $R_3$ is methyl, $R_1$ is trifluoromethyl, p is 1 and $R_4$ is hydrogen.

The absolute configuration of the compounds of the present invention was assigned in agreement with the method described in the PCT International Publication WO2005/080382.

For the remainder of the compounds of the present invention, where stereoisomers were evaluated separately, absolute configuration was assigned based on a reasonable assumption by a skilled person in the art, i.e. absolute configuration was then assigned based on measured binding activity at the dopamine D3 receptor for both enantiomers and comparison with the data of those compounds disclosed in the above cited PCT Publication, which were subjected to detailed analysis.

Further embodiments of the present invention are compounds of formula (IB)' which correspond to the stereochemical isomers of compounds of formula (IB) as defined above enriched in configuration (1S,5R).

In one embodiment, a stereochemical isomer enriched in the (1S,5R) configuration of formula (IB)' or a salt thereof is provided, wherein $R_1$, p, $R_3$ and $R_4$ are as defined for formula (I):

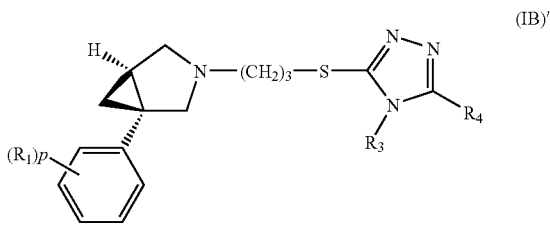

(IB)'

In Formula (IB)', in one embodiment, $R_3$ is methyl, $R_1$ is trifluoromethyl and p is 1. $R_4$ may be an optionally substituted linear or branched alkyl, or an optionally substituted cycloalkyl.

Examples of $R_4$ include methyl, t-butyl, cyclopropyl, cyclopentyl.

In Formula (IB)', in another embodiment, $R_3$ is methyl, $R_1$ is trifluoromethyl and p is 1 and $R_4$ is hydrogen.

Certain of the compounds of the invention may form acid addition salts with one or more equivalents of the acid. The present invention includes within its scope all possible stoichiometric and non-stoichiometric forms.

Pharmaceutical acceptable salts may also be prepared from other salts, including other pharmaceutically acceptable salts, of the compound of formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of structure (I) may exist as polymorphs, which are included in the present invention.

Those skilled in the art will appreciate that in the preparation of the compound of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Certain groups/substituents included in the present invention may be present as isomers. The present invention includes within its scope all such isomers, including racemates, enantiomers, tautomers and mixtures thereof. Certain of the substituted heteroaromatic groups included in compounds of formula (I) may exist in one or more tautomeric forms. The present invention includes within its scope all such tautomeric forms, including mixtures.

In one embodiment of the present invention compounds are provided e a molecular weight of 800 or less. In another embodiment compounds are provided having a molecular weight of 600 or less. Generally, and without being limited thereto, such compounds may have higher oral bioavailability, and sometimes higher solubility and/or brain penetrancy. Molecular weight here refers to that of the unsolvated free base compound, excluding any molecular weight contributed by addition salts, solvent (e.g. water) molecules, prodrug molecular parts cleaved off in vivo, etc.

In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertable in the mammalian (e.g. human) body to the inventive compounds are however included.

Example compounds of the present invention include:
(1S,5R)-3-{3-[(5-cyclopropyl-4-methyl-4H-1,2,4-triazol-3-yl)thio]propyl}-1-[4-(trifluoromethyl)phenyl]-3-azabicyclo[3.1.0]hexane;
(1S,5R)-3-(3-{[5-(1,1-dimethylethyl)-4-methyl-4H-1,2,4-triazol-3-yl]thio}propyl)-1-[4-(trifluoromethyl)phenyl]-3-azabicyclo[3.1.0]hexane;
(1S,5R)-3-{3-[(5-cyclopentyl-4-methyl-4H-1,2,4-triazol-3-yl)thio]propyl}-1-[4(trifluoromethyl)phenyl]-3-azabicyclo[3.1.0]hexane;
(1S,5R)-3-{3-[(4,5-dimethyl-4H-1,2,4-triazol-3-yl)thio]propyl}-1-[4-(trifluoromethyl)phenyl]-3-azabicyclo[3.1.0]hexane;
(1S,5R)-3-{3-[(4-methyl-4H-1,2,4-triazol-3-yl)thio]propyl}-1-[4-(trifluoromethyl)phenyl]-3-azabicyclo[3.1.0]hexane;

or a pharmaceutically acceptable salt thereof.

Some of the compounds of the present invention may be prepared as described in PCT International Publication WO2005/080382.

The present invention also provides a process for preparing a compound of formula (I) or a salt thereof as defined above.

The process of the present invention for preparing compounds of formula (I) in which G is a phenyl derivative, comprises the steps of:

(a) reacting a compound of formula (II):

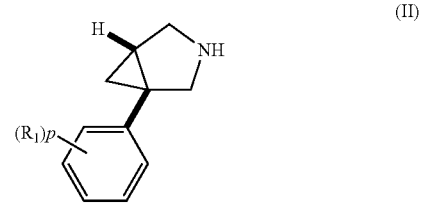

wherein $R_1$ and p are as defined for formula (I), with a compound of formula (III):

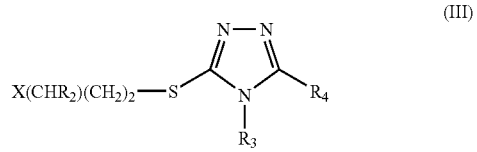

wherein R$_2$, R$_3$ and R$_4$ are as defined for formula (I) and X is a leaving group, or (b) for a compound of formula (I) wherein p is 1 or 2, reacting a compound of formula (IV):

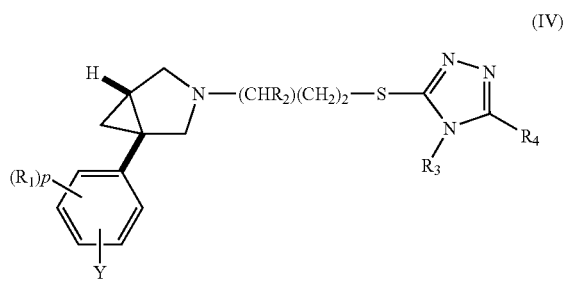

(IV)

wherein R$_1$, R$_2$, R$_3$, and R$_4$ are as defined for formula (I), p is 0 or 1 and Y is halogen, a perfluoroalkylsulfonyloxy group (e.g. trifluoromethylsulfonyloxy), or Y is a group M selected from a boron derivative (e.g. a boronic acid function B(OH)$_2$) or a metal function such as trialkylstannyl (e.g. SnBu$_3$), zinc halide or magnesium halide; with a compound R1-Y1, wherein Y1 is halogen when Y is a group M; or when Y is halogen or a perfluoroalkylsulfonyloxy group Y1 is a group M as defined above or hydrogen that can be activated by a suitable base (e.g. Cs$_2$CO$_3$) in the presence of a suitable transition metal (e.g. Pd); "leaving group" is as understood by a skilled chemist, i.e. a group which can be displaced by a nucleophile in e.g. a S$_N$2, S$_N$1 or S$_N$Ar type reaction;

and thereafter optionally for process (a) or process (b):

(i) removing any protecting group(s); and/or (ii) forming a salt; and/or (iii) converting a compound of formula (I) or a salt thereof to another compound of formula (I) or a salt thereof.

Process (a) may be performed using conventional methods for the formation of a tertiary amine. The leaving group X can be halogen such as chlorine. Alternatively X can be a sulfonyloxy group such C$_{1-4}$alkylsulfonyloxy (e.g. methanesulfonyloxy), C$_{1-4}$alkylsulfonyloxy or haloC$_{1-4}$alkylsulfonyloxy (e.g. trifluoromethanesulfonyloxy); or arylsulfonyloxy wherein aryl is optionally substituted phenyl, an optionally substituted 5- or 6-membered heteroaromatic group, or an optionally substituted bicyclic group, for example optionally substituted phenyl, wherein in each case the optional substituents are one or more C$_{1-2}$alkyl groups; e.g. para-toluenesulfonyloxy. When X is a halogen the reaction may be carried out using a base such as potassium carbonate in the presence of a source of iodide such as sodium iodide in a solvent such as N,N-dimethylformamide at a suitable temperature, e.g. 60° C.

Compounds of formula (II) may be prepared by methods well known in the art (e.g. *J. Med. Chem.* 1981, 24, 481-490). Interconversion of groups R$_1$ may be affected by methodology well known in the art (e.g. demethylation of a methoxy group resulting in a hydroxy group using a suitable Lewis acidic reagent such as boron tribromide in an inert solvent such as dichloromethane).

Reaction of a compound of formula (IV) with R1-Y1 according to process (b) may be effected in the presence of a transition metal e.g., palladium catalyst such as bis-triphenylphosphinepalladium dichloride, tetrakis-triphenylphosphinepalladium (0) or the complex formed in situ from tris(dibenzylideneacetone) dipalladium(0) and 4,5-bis(diphenylphosphino)-9,9-dimethylxanthene. When M is a boronic acid function such as B(OH)$_2$ the reaction may be carried out under basic conditions, for example using aqueous sodium carbonate in a suitable solvent such as dioxane. When M is trialkylstannyl the reaction may be carried out in an inert solvent, such as xylene or dioxane optionally in the presence of LiCl. When M is a zinc or magnesium halide the reaction may be effected in an aprotic solvent such as tetrahydrofuran. When M is hydrogen that can be activated by a suitable base (e.g. Cs$_2$CO$_3$) in the presence of a suitable transition metal (e.g. Pd) the reaction may be carried out in an inert solvent such as dioxane in the presence of a suitable base such as Cs$_2$CO$_3$. The substituent Y may be halogen such as bromine, or a sulfonyloxy group such as trifluoromethylsulfonyloxy; and Y1 is may be a group M, such as hydrogen that can be activated by a suitable base (e.g. Cs$_2$CO$_3$) in the presence of a suitable transition metal (e.g. Pd).

In one aspect of the present invention there is provided a synthetic process for the preparation of compounds of formula (II). The process may be conveniently performed also for preparing compounds of formula (IIa), in which the phenyl moiety is replaced by pyridine. This process comprises the following steps:

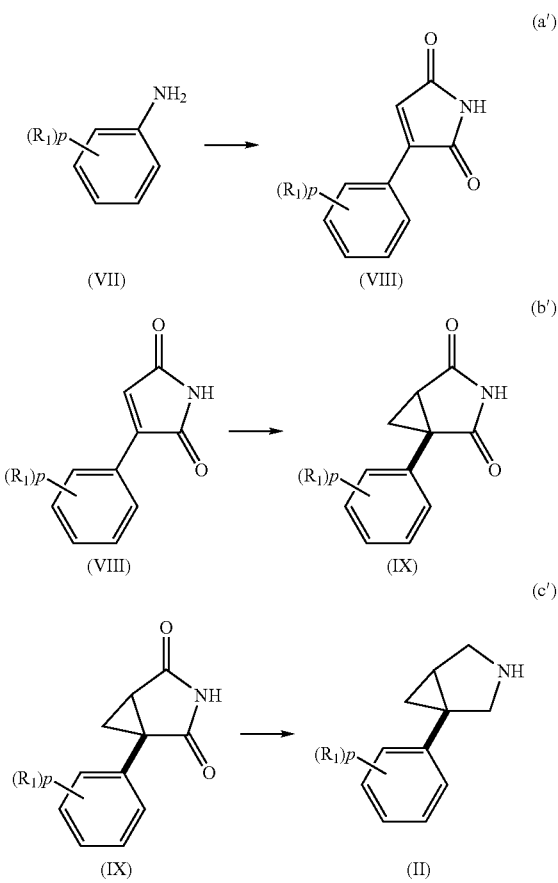

wherein:

step (a') means diazotation of an aniline (VII) followed by reaction with maleimide to give 3-arylmaleimide (VIII);

step (b') means cycloropanation of (VIII) to provide bicyclic imide (IX);

step (c') means reduction of imide (IX) to give compounds of formula (II).

Step (a') may be effected using conventional methods for the Meerwein reaction (e.g. *J. Am. Chem. Soc.* 1955, 77, 2313 describes the formation of arylmaleimides using this approach). Alternatively, in many cases this step is suitably performed applying a procedure where to a mixture of maleimide, an appropriate copper (II) salt such as anhydrous CuCl$_2$, and a suitable organonitrite, such as tert-butyl nitrite, in a compatible solvent, such as acetonitrile, is slowly added a solution of a compound of formula (VII). This is followed by allowing time to react as appropriate and a suitable workup.

Step (b') consists of slow addition of a solution of purified compound of formula (VIII), or mixtures containing a compound of formula (VIII), dissolved in a suitable solvent such as dimethylsulfoxide, to a solution of trimethylsulfoxonium iodide in a suitable solvent such as dimethylsulfoxide and a suitable base, such as sodium hydride. This is followed by allowing time to react as appropriate and a suitable workup.

Step (c') can be performed using a suitable reducing agent in a compatible solvent, such as borane in tetrahydrofuran or Red-Al® in toluene at an appropriate temperature, such as for example 65° C. in the case of borane as the reducing agent. This is followed by a suitable workup.

In another aspect of the present invention an alternative synthetic process for the preparation of compounds of formula (II), or generally of formula (XIII), is provided. This process comprises the following steps:

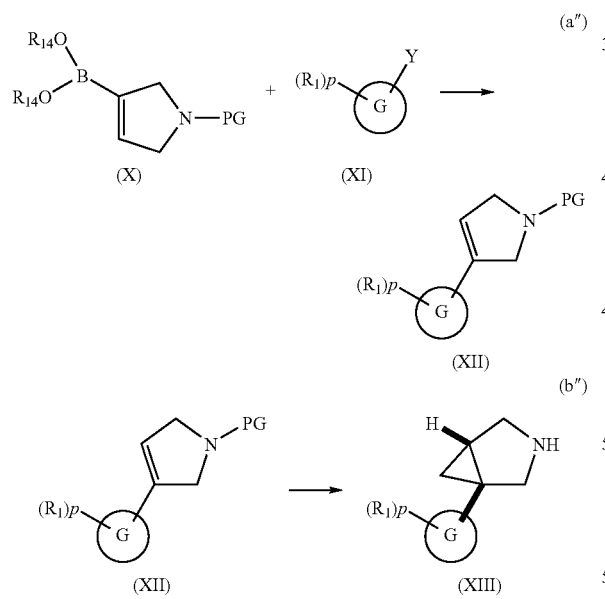

wherein:

R$_1$, p and G are as defined for formula (I), R$_{14}$O is a suitable alkoxy group, PG is an appropriate protecting group and Y may be halogen such as bromine, or a sulfonyloxy group such as trifluoromethylsulfonyloxy and comprising the following steps:

step (a″) means coupling reaction of a (2,5-dihydro-1H-pyrrol-3-yl)boronate (X) with the aromatic halogen or sulfonyloxy derivative (XI);

step (b″) means cycloropanation of (XII) followed by, if appropriate, deprotection to provide bicyclic amine (XIII).

Step (a″) may be effected using conventional methods for the Suzuki coupling, e.g. using tetrakis(triphenylphosphine) palladium(0) as the source of catalytic palladium(0) in the presence of cesium fluoride in an appropriate solvent such as tetrahydrofuran at a suitable temperature. (R$_{14}$O)$_2$B may suitably be 4,4,5,5-tetramethyl-1,3,2-dioxaborolan-2-yl and PG benzyl, representing a compound of structure (X) as reported in *Synlett* 2002, 5, 829-831.

Step (b″) consists of a cyclopropanation reaction effected for example using the reagent generated from trimethylsulfoxonium iodide and a suitable base such as sodium hydride. This is followed by a deprotection reaction.

A compound of formula (III) may itself be prepared by reacting a compound of formula (V):

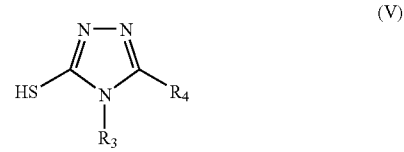

wherein R$_3$ and R$_4$ are as hereinbefore defined; with a compound of formula (VI):

$$L(CHR_2)(CH_2)_2X \qquad (VI)$$

wherein X is defined as for formula (I) and L is a leaving group, e.g., a bromine atom. according to typical reaction conditions described in the literature.

Compounds of formula (V) and (VI) are commercially available or may be prepared through reactions known in the literature.

Compounds of formula (I) where R$_1$, R$_2$, R$_3$, R$_4$, G and p are as above defined may be prepared by reacting a compound of formula (XIV):

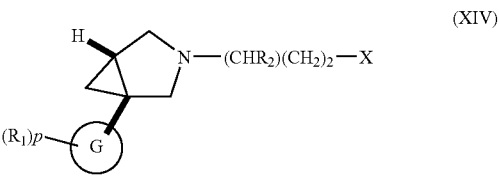

wherein R$_1$, R$_2$, G and p are as defined for formula (I) and X is a leaving group, with a compound of formula (V):

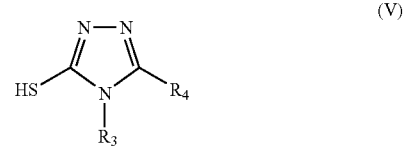

wherein R$_3$ and R$_4$ are as hereinbefore defined.

A compound of formula (XIV) wherein R$_1$, G and p are as defined for formula (I), X is a leaving group and R$_2$ is H (hydrogen) can be prepared by alkylation of a compound of formula (XIII) in the presence of a suitable base such as a tertiary amine, for example diisopropylethylamine, with a propyl derivative carrying two leaving groups of preferably differential reactivity in positions 1 and 3, for example 1-bromo-3-chloropropane.

A compound of formula (XIV) wherein $R_1$, G and p are as defined for formula (I), X is a leaving group and $R_2$ is $C_{1-4}$alkyl can be prepared by the reaction between a beta-hydroxy ketone, for example 4-hydroxy-2-butanone if $R_2$ is methyl, with a compound of formula (XIII) in the presence of a suitable borohydride source such as $NaBH(OAc)_3$, followed by conversion of the hydroxyl group into a leaving group by methods known to the person skilled in the art, for example by the action of thionyl chloride.

Interconversion reactions between compounds of formula (I) and salts thereof may be performed using methods well known in the art. Examples include:

(i) converting one or more of $R_1$ from alkoxy (e.g. methoxy) to hydroxy, (ii) converting one or more of $R_1$ from hydroxy to sulfonyloxy, such as alkylsulfonyloxy or haloalkylsulfonyloxy, e.g. methanesulfonyloxy or alkylsulfonyloxy or trifluoro-methanesulfonyloxy, (iii) converting one or more of $R_1$ from halogen or perfluoro-alkylsulfonyloxy to cyano;

and optionally thereafter forming a salt of formula (I).

Compounds of formula (I) have been found to exhibit affinity for dopamine receptors, in particular the $D_3$ receptor, and are expected to be useful in the treatment of disease states which require modulation of such receptors, such as psychotic conditions. Such affinity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In the context of the present invention pKi (corresponding to the antilogarithm of Ki) is used instead of Ki and the compounds of the present invention typically show pKi greater than 7. In one aspect the present invention provides compounds of formula (I) having a pKi comprised between 7 and 8. In another aspect, the present invention provides compounds of formula (I) having a pKi between 8 and 9. In a further aspect the present invention provides compounds of formula (I) having a pKi greater than 9.

Many of the compounds of formula (I) have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. It has been suggested that blockade of the recently characterised dopamine $D_3$ receptor may give rise to beneficial antipsychotic activity without significant eps. (see for example Sokoloff et al, Nature, 1990; 347: 146-151; and Schwartz et al, Clinical Neuropharmacology, Vol 16, No. 4, 295-314, 1993). In one embodiment compounds of the present invention are provided which have higher (e.g. $\geq 10\times$ or $\geq 100\times$ higher) affinity for dopamine $D_3$ than dopamine $D_2$ receptors (such affinity can be measured using standard methodology for example using cloned dopamine receptors—see herein). Said compounds may suitably be used as selective modulators of $D_3$ receptors.

From the localisation of $D_3$ receptors, it could also be envisaged that the compounds could also have utility for the treatment of substance abuse where it has been suggested that $D_3$ receptors are involved (e.g. see Levant, 1997, Pharmacol. Rev., 49, 231-252). Examples of such substance abuse include alcohol, cocaine, heroin and nicotine abuse. Other conditions which may be treated by the compounds include dyskinetic disorders such as Parkinson's disease, neuroleptic-induced parkinsonism and tardive dyskinesias; depression; anxiety, cognitive impairment including memory disorders such as Alzheimers disease, sexual dysfunction, sleep disorders, emesis, movement disorders, amnesia, aggression, autism, vertigo, dementia, circadian rhythm disorders and gastric motility disorders e.g. IBS.

Other conditions which may be treated with the compounds of the invention include obsessive compulsive (OC) spectrum disorders as below defined.

Compounds of formula (I) may be used for treatment of all aspects of drug dependency including withdrawal symptoms from drugs of abuse such as alcohol, cocaine, opiates, nicotine, benzodiazepines and inhibition of tolerance induced by opioids. In addition, compounds of formula (I) and pharmaceutically acceptable salts and solvates thereof may be used to reduce craving and therefore will be useful in the treatment of drug craving. Drug craving can be defined as the incentive motivation to self-administer a psychoactive substance that was previously consumed. Three main factors are involved in the development and maintenance of drug craving: (1) Dysphoric states during drug withdrawal can function as a negative reinforcer leading to craving; (2) Environmental stimuli associated with drug effects can become progressively more powerful (sensitization) in controlling drug seeking or craving, and (3) A cognition (memory) of the ability of drugs to promote pleasurable effects and to alleviate a dysphoric state during withdrawal. Craving may account for the difficulty that individuals have in giving up drugs of abuse and therefore contributes significantly to the development and maintenance of drug dependence.

The compounds of formula (I) are of potential use as antipsychotic agents for example in the treatment of schizophrenia, schizo-affective disorders, psychotic depression, mania, paranoid and delusional disorders. Furthermore, they could have utility as adjunct therapy in Parkinsons Disease, particularly with compounds such as L-DOPA and possibly dopaminergic agonists, to reduce the side effects experienced with these treatments on long term use (e.g. see Schwartz et al., Brain Res. Reviews, 1998, 26, 236-242).

Compounds of formula (I) may be used for the treatment of obsessive compulsive disorders (OCD) and of psychiatric and neuropsychiatric disorders related to them (OC spectrum disorders).

Compounds of formula (I) may be useful in the treatment of sexual dysfunction, such as premature ejaculation.

Compounds of formula (I) may be useful for the treatment of cognition impairment.

Within the context of the present invention, the terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term "psychotic disorder" includes:

Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

Within the context of the present invention, the term "substance-related disorder" includes:—

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

Within the context of the present invention, the term "obsessive compulsive spectrum disorder" includes:

Obsessive compulsive disorders (300.3), somatoform disorders including body dysmorphic disorder (300.7) and hyperchondriasis (300.7), bulimia nervosa (307.51), anorexia nervosa (307.1), eating disorders not elsewhere classified (307.50) such as binge eating, impulse control disorders not elsewhere classified (including intermitted explosive disorder (312.34), compulsive buying or shopping, repetitive self-mutilation, onychophagia, psychogenic excoriation, kleptomania (312.32), pathological gambling (312.31), trichotillomania (312.39) and internet addiction), paraphilia (302.70) and nonparaphilic sexual addictions, Sydeham's chorea, torticollis, autistic disorders (299.0), compulsive hoarding, and movement disorders, including Tourette's syndrome (307.23).

Within the context of the present invention, the term "sexual dysfunction" includes also premature ejaculation (302.75).

Within the present invention the term "cognition impairment" includes cognition impairment in other diseases such as schizophrenia, bipolar disorder, depression, other psychiatric disorders and psychotic conditions associated with cognitive impairment, e.g. Alzheimer's disease.

In a further aspect therefore the present invention provides a method of treating a condition for which modulation [especially inhibition/antagonism (which may also translate into inverse agonism in constitutively active receptor systems)] of dopamine receptors (especially dopamine $D_3$ receptors) is beneficial, which comprises administering to a mammal (e.g. human) in need thereof an effective amount of a compound of formula (I) or a pharmaceutically (i.e physiologically) acceptable salt thereof.

Thus, a still further aspect the invention provides a method of treating a psychotic condition (e.g. schizophrenia) or substance abuse or obsessive compulsive spectrum disorders (such as binge eating) or sexual dysfunctions (such as premature ejaculation) which comprises administering to a mammal (e.g. human) in need thereof an effective amount of a compound of formula (I) as herein defined or a pharmaceutically acceptable salt thereof.

The invention also provides a compound of formula (I) or a pharmaceutically acceptable salt thereof for use in therapy.

The invention also provides a compound of formula (I) or a pharmaceutically acceptable salt thereof for use in the treatment of a condition in a mammal for which modulation [especially inhibition/antagonism (which may also translate into inverse agonism in constitutively active receptor systems)] of dopamine receptors (especially dopamine $D_3$ receptors) is beneficial.

The invention also provides the use of a compound of formula (I) or a pharmaceutically acceptable salt thereof in the manufacture of a medicament for the treatment of a condition in a mammal for which modulation [especially inhibition/antagonism (which may also translate into inverse agonism in constitutively active receptor systems)] of dopamine receptors (especially dopamine $D_3$ receptors) is beneficial.

In one embodiment, $D_3$ antagonists according to the present invention are used in the treatment of psychoses such as schizophrenia, in the treatment of substance abuse, in the treatment of obsessive compulsive spectrum disorders, in the treatment of sexual dysfunction and in the treatment of cognition impairment.

Also provided is the use of a compound of formula (I) or a pharmaceutically acceptable salt thereof in the manufacture of a medicament for the treatment of a psychotic condition (e.g. schizophrenia), substance abuse in a mammal, obsessive compulsive spectrum disorders, sexual dysfunctions and cognition impairment.

Also provided is a compound of formula (I) or a pharmaceutically acceptable salt thereof for use in the treatment of a psychotic condition (e.g. schizophrenia), substance abuse, obsessive compulsive spectrum disorders, sexual dysfunction and cognition impairment in a mammal.

Also provided is a compound of formula (I) or a pharmaceutically acceptable salt thereof for use as an active therapeutic substance in a mammal, e.g. for use in the treatment of any of the conditions described herein.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of formula (I) or a pharmaceutically (i.e physiologically) acceptable salt thereof and a pharmaceutically (i.e physiologically) acceptable carrier. The pharmaceutical composition can be for use in the treatment of any of the conditions described herein.

The compounds of formula (I) may be administered by any convenient method, for example by oral, parenteral (e.g. intravenous), buccal, sublingual, nasal, rectal or transdermal administration and the pharmaceutical compositions adapted accordingly.

The compounds of formula (I) and their pharmaceutically acceptable salts which are active when given orally can be formulated as liquids or solids, for example syrups, suspensions or emulsions, tablets, capsules and lozenges.

A liquid formulation will generally consist of a suspension or solution of the compound or pharmaceutically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochloro-hydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment, the composition is in unit dose form such as a tablet, capsule or ampoule.

Each dosage unit for oral administration contains for example from 1 to 250 mg (and for parenteral administration contains for example from 0.1 to 25 mg) of a compound of the formula (I) or a pharmaceutically acceptable salt thereof calculated as the free base.

The pharmaceutically acceptable compounds of the invention will normally be administered in a daily dosage regimen (for an adult patient) of, for example, an oral dose of between 1 mg and 500 mg, for example between 10 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a pharmaceutically acceptable salt thereof calculated as the free base, the compound being administered 1 to 4 times per day. Suitably the compounds will be administered for a period of continuous therapy, for example for a week or more.

Biological Test Methods

Functional potency and intrinsic activity of compounds of this invention can be measured by the following GTPγS scintillation proximity assay (GTPγS-SPA). Cells used in the study are Chinese Hamster Ovary (CHO) Cells.

Cell Line

CHO_D2

CHO_D3

Cell membranes are prepared as follows. Cell pellets are resuspended in 10 volumes of 50 mM HEPES, 1 mM EDTA pH 7.4, using KOH. On the day the following proteases are added to the buffer just prior to giving the homogenisation buffer.

$10^{-6}$M Leupeptin (Sigma L2884)–5000×stock=5 mg/ml in buffer 25 ug/ml Bacitracin (Sigma B0125)–1000×stock=25 mg/ml in buffer 1 mM PMSF–1000×stock=17 mg/ml in 100% ethanol $2 \times 10^{-6}$M Pepstain A–1000×stock=2 mM in 100% DMSO The cells are homogenised by 2×15 second bursts in a 1 litre Glass Waring blender in a class two biohazard cabinet. The resulting suspension is spun at 500 g for 20 mins (Beckman T21 centrifuge: 1550 rpm). The supernatant is withdrawn with a 25 ml pipette, aliquotted into pre-chilled centrifuge tubes and spun at 48,000 g to pellet membrane fragments (Beckman T1270: 23,000 rpm for 30 mins). The final 48,000 g pellet is resuspended in Homogenisation Buffer, (4× the volume of the original cell pellet). The 48,000 g pellet is resuspended by vortexing for 5 seconds and homogenized in a dounce homogenizer 10-15 stokes. The prep is distributed into appropriate sized aliquots, (200-1000 ul), in polypropylene tubes and store at −80° C. Protein content in the membrane preparations is evaluated with the Bradford protein assay.

The final top concentration of test drug is 3 uM in the assay and 11 points serial dilution curves 1:4 in 100% DMSO are carried out using a Biomek FX. The test drug at 1% total assay volume (TAV) is added to a solid, white, 384 well assay plate. 50% TAV of precoupled (for 90 mins at 4° C.) membranes, 5 μg/well, and Wheatgerm Agglutinin Polystyrene Scintillation Proximity Assay beads (RPNQ0260, Amersham), 0.25 mg/well, in 20 mM HEPES pH 7.4, 100 mM NaCl, 10 mM MgCl$_2$, 60 μg/ml saponin and 30 μM GDP is added. The third addition was a 20% TAV addition of either buffer, (agonist format) or EC$_{80}$ final assay concentration of agonist, Quinelorane, prepared in assay buffer (antagonist format). The assay was started by the addition of 29% TAV of GTPγ[$^{35}$S] 0.38 nM final (37 MBq/ml, 1160 Ci/mmol, Amersham). After all additions assay plates are spun down for 1 min at 1,000 rpm. Assay plates are counted on a Viewlux, 613/55 filter, for 5 min., between 2-6 hours after the final addition.

The effect of the test drug over the basal generates EC$_{50}$ value by an iterative least squares curve fitting programme, expressed in the table as pEC$_{50}$ (i.e. −logEC$_{50}$). The ratio between the maximal effect of the test drug and the maximal effect of full agonist, Quinelorane, generates the Intrinsic Activity (IA) value (i.e. IA=1 full agonist, IA<1 partial agonist). fpKi values of test drug are calculated from the IC$_{50}$ generated by "antagonist format" experiment, using Cheng & Prusoff equation: fKi=IC$_{50}$/1+([A]/EC$_{50}$) where: [A] is the concentration of the agonist 5-HT in the assay and EC$_{50}$ is the 5-HT EC$_{50}$ value obtained in the same experiment. fpKi is defined as −logfKi.

The compounds of the invention listed above have pKi values within the range of 7.0-10.5 at the dopamine D3 receptor. pKi results are only estimated to be accurate to about ±0.3-0.5.

The compounds of the invention listed above have a selectivity over D2 greater than 30.

EXAMPLES

The invention is further illustrated by the following non-limiting examples.

All temperatures refer to ° C. Infrared spectra were measured on a FT-IR instrument. Compounds were analysed by direct infusion of the sample dissolved in acetonitrile into a mass spectra operated in positive electro spray (ES+) ionisation mode. Proton Magnetic Resonance ($^1$H-NMR) spectra were recorded at 400 MHz, chemical shifts are reported in ppm downfield (d) from Me$_4$Si, used as internal standard, and are assigned as singlets (s), broad singlets (bs), doublets (d), doublets of doublets (dd), triplets (t), quartets (q) or multiplets (m).

Optical rotations were measured using a (Perkin Elmer Model 241) polarimeter operating at 589 nm (Sodium source). Measurements were made using a 1 decimeter microcell thermostated at 23° C. Concentrations were typically 10 mg/ml (c=0.01). For ab initio OR assignments, the Dalton Quantum Chemistry Program was used.

Column chromatography was carried out over silica gel (Merck AG Darmstadt, Germany). The following abbreviations are used in the text: HOBt=1-hydroxybenzotriazole EtOAc=ethyl acetate, Et$_2$O=diethyl ether, THF=tetrahydrofuran, Tlc refers to thin layer chromatography on silica plates, and dried refers to a solution dried over anhydrous sodium sulphate, r.t. (RT) refers to room temperature, Rt=retention time, DMSO=dimethyl sulfoxide.

Description 1: 3-[4-(trifluoromethyl)phenyl]-1H-pyrrole-2,5-dione (P1)

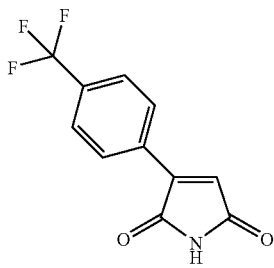

A mixture of hydrochloric acid (37%, 285 mL) and water (190 mL) was added to 4-(trifluoromethyl)aniline (150 g, 116 mL) at room temperature with vigorous stirring and the formed precipitate was allowed to stir for further 30 minutes. Temperature was reduced to 0° C. and sodium nitrite (70.6 g) in 180 mL of water was added dropwise to the stirred suspension. At the end of diazotisation, a clear yellow solution was obtained. Maleimide (180 g) in acetone (1.1 L) was added dropwise at 0° C. and then the pH of the solution was adjusted to 3-3.5 by adding sodium acetate. Copper (II) chloride (18.8 g) was added to the vigorously stirred mixture. After a few minutes a gas started to develop (conspicuous foaming). The reaction mixture was allowed to stir at 0° C. for 1 h and overnight at room temperature. Acetone was removed in vacuo, the residue was filtered and dried overnight in vacuo to give the title compound (155 g) as a light brown solid.

MS (m/z): 242.2 [MH]$^+$.

Description 2: (1R,5S/1S,5R)-1-[4-(trifluoromethyl)phenyl]-3-azabicyclo[3.1.0]-hexane-2,4-dione (P2)

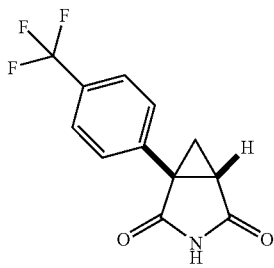

Milled sodium hydroxide (40 g) was added in small portions to a stirred solution of trimethylsulfoxonium iodide (219 g) in DMSO (anhydrous, 2 L). The resulting mixture was allowed to stir at room temperature for 1.5 h. 3-[4-(Trifluoromethyl)phenyl]-1H-pyrrole-2,5-dione (P1, 120 g) dissolved in DMSO (anhydrous, 0.5 L) was then added dropwise and the resulting mixture was allowed to stir at room temperature for 20 minutes. Temperature was then reduced to 0° C. and NH$_4$Cl (aqueous saturated solution, 2 L) was slowly added, followed by Et$_2$O (1 L). After separation of the two phases, the aqueous layer was repeatedly extracted with Et$_2$O (3×1 L). Combined organic layers were washed with brine (2×1 L) and then dried over Na$_2$SO$_4$. Evaporation of the solvent gave a light brown solid which was suspended in 1 L of dichloromethane and 1 L of cyclohexane. The mixture was allowed to stir at room temperature for 45 minutes and then filtered to give the title compound (116 g) as white solid.

MS (m/z): 256.1 [MH]$^+$.

Description 3: (1R,5S/1S,5R)-1-[4-(trifluoromethyl)phenyl]-3-azabicyclo[3.1.0]hexane (P3)

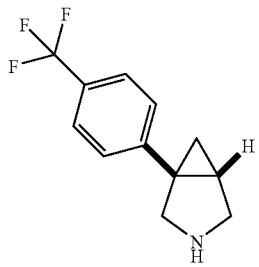

Borane (1M in tetrahydrofuran, 1.4 l) was charged into a 5 l reactor under N$_2$ and cooled at 0° C. (1R,5S/1S,5R)-1-[4-(trifluoromethyl)phenyl]-3-azabicyclo[3.1.0]hexane-2,4-dione (P2, 101 g) dissolved in tetrahydrofuran (anhydrous, 1 L) was then added dropwise with vigorous stirring whereby the temperature was constantly kept below 5° C. and gas evolution was monitored. At the end of the addition the resulting mixture was allowed to stir at 0° C. for 1 h and then at room temperature overnight. The mixture was then cooled to 0° C. and methanol (200 mL) followed by hydrochloric acid (6 M solution, 0.8 L) were cautiously added monitoring gas evolution. tetrahydrofuran was then removed in vacuo, the residue was cooled to 0° C. and sodium hydroxide (5 M solution) was added until pH 9-10 had been reached. The aqueous layer was extracted with Et$_2$O (3×1 L). Removal of solvent in vacuo gave the title compound (140 g) as colorless oil.

MS (m/z): 228.1 [MH]$^+$.

Description 4: (1S,5R)-1-[4-(trifluoromethyl)phenyl]-3-azabicyclo[3.1.0]hexane (P4)

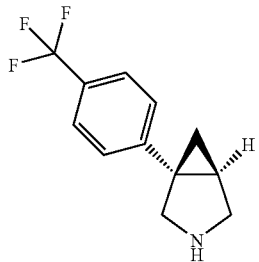

(S)-(+)-Mandelic acid (94 g) was added in portions to a stirred solution of (1R,5S/1S,5R)-1-[4-(trifluoromethyl)phenyl]-3-azabicyclo[3.1.0]hexane (P3, 140 g) in 1.4 L of tetrahydrofuran. The resulting mixture was stirred at room temperature for 2 h until a white precipitate was formed. The mixture was then warmed up to reflux temperature, stirred for 45 minutes and then slowly cooled down to room temperature. The white solid was collected by filtration and dried in vacuo. This material was recrystallised 4 times from tetrahydrofuran (10 volumes) to give 32.5 g of a white solid. This material was then suspended in sodium hydroxide (1M solution, 400 mL) and Et$_2$O (400 mL) and allowed to stir at room temperature until complete dissolution. After separation of the two phases, the aqueous layer was extracted again with Et$_2$O (3×250 mL). Combined organic layers were washed with sodium hydroxide (1M solution, 3×200 mL) and then dried over Na$_2$SO$_4$. Evaporation of solvent in vacuo gave the title compound (19 g) as white solid. The absolute configuration of the optical isomers was assigned as described in PCT International Publication WO2005/080382.

NMR (¹H, CDCl₃): δ 7.51 (d, 2H), 7.25 (d, 2H), 3.20 (d, 1H), 3.0-3.1 (m, 3H), 1.69 (m, 1H), 0.8-1.0 (m, 2H), NH not observed. MS (m/z): 228.1 [MH]⁺.

Analytical Chromatography

Column: chiralcel OD 10 um, 250×4.6 mm

Mobile Phase: A: n-Hexane; B: Isopropanol+0.1% Isopropyl amine

Gradient: isocratic 2% B

Flow Rate: 1 mL/min

UV Wavelength Range: 200-400 nm

Analysis Time 25 min ret. time (min) % a/a 16.5  0.4  (1R,5S)-1-[4-(trifluoromethyl)phenyl]-3-azabicyclo[3.1.0]hexane 21.7  99.6  title compound Specific Optical Rotation: [α]$_D$=−10° (CDCl₃, T=20° C., c≅0.004 g/0.8 mL).

Description 5: (1S,5R)-3-(3-chloropropyl)-1-[4-(trifluoromethyl)phenyl]-3-azabicyclo[3.1.0]hexane (P5)

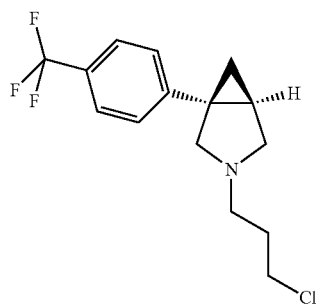

To a solution of (1S,5R)-1-[4-(trifluoromethyl)phenyl]-3-azabicyclo[3.1.0]hexane (P4, 1.00 g) in dry tetrahydrofuran (5 mL), diisopropylethylamine (2.4 mL) and 1-bromo-3-chloropropane (3.7 mL) were added and the resulting mixture was heated at reflux for 3 hours. After cooling at room temperature the mixture was diluted with ethyl acetate (30 mL) washed twice with a saturated solution of NH₄Cl in water (20 mL) and once with a saturated solution of NaHCO₃ in water (20 mL), dried over anhydrous Na₂SO₄ and concentrated under reduced pressure. The crude product was purified by silica gel chromatography eluting with cyclohexane/EtOAc 7:3 to give the title compound as a colourless oil (1.26 g).

NMR (¹H, CDCl₃): δ 7.50 (d, 2H) 7.19 (d, 2H), 3.59 (t, 2H), 3.33 (d, 1H), 3.09 (d, 1H), 2.58 (m, 2H), 2.66 (dd, 1H), 2.46 (dd, 1H), 1.92 (m, 2H), 1.74 (m, 1H), 1.67 (t, 1H), 0.81 (dd, 1H). MS (m/z): 304 [MH]⁺.

Description 6: 5-cyclopropyl-4-methyl-2,4-dihydro-3H-1,2,4-triazole-3-thione (P6)

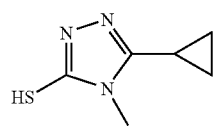

Cyclopropanecarboxylic acid (1 g), N-methylhydrazinecarboxamide (1.2 g), 1-(3-dimethylaminopropyl)-3-ethyl carbodiimide hydrochloride (2.23 g), HOBt (0.078 g) and triethylamine (1.77 mL) were dissolved, under nitrogen, in dry THF (30 mL) at room temperature. The mixture was stirred overnight, then THF was removed under vacuum. NaOH (1 M, 13 mL) was added and mixture was heated at 80° C. for 5 h. The reaction mixture was cooled to 0° C. and acidified to ca. pH 1 with HCl 1M. The suspended product was isolated by filtration, washing with water (2×3 mL). The cake was dried at room temperature overnight under vacuum to give the title compound (0.86 g).

NMR (¹H, CDCl₃): δ 11.3 (bs, SH), 3.80 (s, 3H), 1.75 (m, 1H), 1.05 (m, 4H). MS (m/z): 156.1 [MH]⁺.

Description 7: 5-(1,1-Dimethylethyl)-4-methyl-2,4-dihydro-3H-1,2,4-triazole-3-thione (P7)

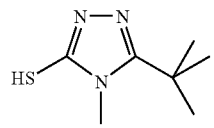

To a suspension of 4-methyl-3-thiosemicarbazide (0.53 g) in dichloromethane (10 mL) and triethylamine (0.73 mL) was added slowly via syringe pivaloyl chloride (5 mmol). Formation of a precipitate was observed. The mixture was kept overnight. Volatiles were evaporated in vacuo, the residue heated to 80° C. in aqueous NaOH (1 M, 25 mL) for 3 h. Aqueous HCl (2 M) was then added at 25° C. until pH ca. 6. The mixture was concentrated to dryness, water (10 mL) was added and the product collected by filtration, washing with saturated aqueous NaHCO₃ (2.5 mL) and then water (10 mL) to give, after drying, the title compound (0.23 g) of ca. 90% purity by NMR as a colourless solid.

NMR (¹H, CDCl₃): δ 11.0 (bs, 1H), 3.7 (s, 3H), 1.4 (s, 9H). MS (m/z): 172 [M+H]⁺.

General Procedures to Examples 1-3

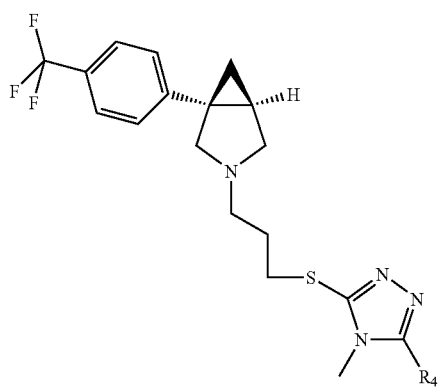

To a solution of the respective 3-thio-5-R₄-1,2,4-triazole (0.16 mmol) in dry acetonitrile (2 mL) 2-tert-butylimino-2-diethylamino-1,3-dimethyl-perhydro-1,3,2-diaza-phosphorine on polystyrene (90 mg, 2.2 mmol/g) was added and the resulting mixture was shaken for 1 h at room temperature, then (1S,5R)-1-(4-bromophenyl)-3-(3-chloropropyl)-3- azabicycle-[3.1.0]hexane (P5, 40 mg) was added and the resulting mixture was shaken at 50° C. overnight. After cooling the resin was removed by filtration, washed with dichloromethane (2 mL) and methanol (2 mL) and the collected liquid phase was evaporated under reduced pressure. Two isomers were formed by S- and N-alkylation, the major isomer being the desired S-alkylated. Those isomers were separated using mass directed HPLC using a Waters XTerra Prep MS C18 10 μm, 30×150 mm column using the following conditions:

|  | Time | Flow | % A | % B |
|---|---|---|---|---|
| Prerun | 0 | 40 ml/min | 99 | 1 |
|  | 1 | 40 ml/min | 99 | 1 |
| Run | 0 | 40 ml/min | 99 | 1 |
|  | 10 | 40 ml/min | 75 | 25 |
|  | 14.5 | 40 ml/min | 10 | 90 |
|  | 15 | 40 ml/min | 0 | 100 |
| Postrun | 0 | 40 ml/min | 0 | 100 |
|  | 0.2 | 45 ml/min | 0 | 100 |
|  | 1.5 | 45 ml/min | 0 | 100 |
|  | 2 | 40 ml/min | 0 | 100 |

A = H2O + 0.1% formic acid

B = acetonitrile + 0.1% formic acid

Then solvent was removed under reduced pressure to give title compounds as formate salts.

The S-alkylated isomers were dissolved in dry diethyl ether and cooled at 0° C. 1.2 eq of HCl (1.0 M solution in diethyl ether) were slowly added. The resulting precipitate was decanted, washed with pentane and filtered, yielding the products as the hydrochloride salts.

Example 1

(1S,5R)-3-{3-[(5-cyclopropyl-4-methyl-4H-1,2,4-triazol-3-yl)thio]propyl}-1-[4-(trifluoromethyl)phenyl]-3-azabicyclo[3.1.0]hexane hydrochloride (E1)

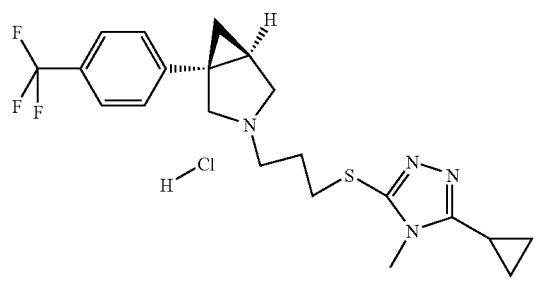

NMR ($^1$H, methanol-d4): δ 7.66 (d, 2H), 7.51 (d, 2H), 4.15 (d, 1H), 3.87 (d, 1H), 3.79 (m, 3H), 3.67 (m, 2H), 3.45 (t, 2H), 3.39 (t, 2H), 2.31 (m, 3H), 2.23 (m, 1H), 1.59 (m, 1H), 1.37 (m, 2H), 1.31 (m, 1H), 1.19 (m, 2H). MS (m/z): 423.2 [MH]$^+$.

Example 2

(1S,5R)-3-(3-{[5-(1,1-dimethylethyl)-4-methyl-4H-1,2,4-triazol-3-yl]thio}propyl)-1-[4-(trifluoromethyl)phenyl]-3-azabicyclo[3.1.0]hexane hydrochloride (E2)

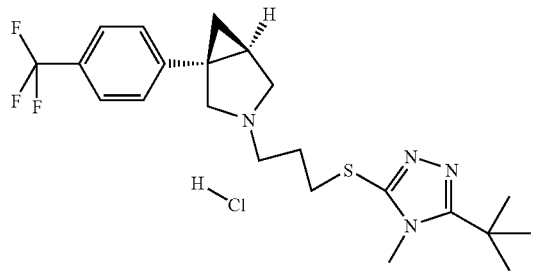

NMR ($^1$H, methanol-d4): δ 7.66 (d, 2H), 7.51 (d, 2H), 4.15 (d, 1H), 3.88 (m, 1H), 3.87 (s, 3H), 3.67 (m, 2H), 3.47 (t, 2H), 3.42 (t, 2H), 2.32 (m, 3H), 1.62 (m, 1H), 1.56 (s, 9H), 1.33 (m, 1H). MS (m/z): 439 [MH]$^+$.

Example 3

(1S,5R)-3-{3-[(5-cyclopentyl-4-methyl-4H-1,2,4-triazol-3-yl)thio]propyl}-1-[4(trifluoromethyl)phenyl]-3-azabicyclo[3.1.0]hexane hydrochloride (E3)

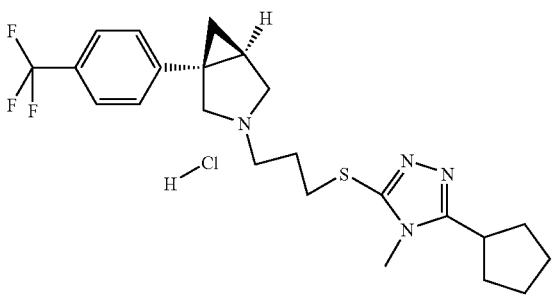

NMR ($^1$H, DMSO-D6): δ 10.61 (bs, 1H), 7.70 (d, 2H), 7.51 (d, 2H), 4.04 (m, 1H), 3.54 (m, 3H), 3.44 (m, 8H), 2.31 (m, 1H), 2.15 (m, 2H), 2.02 (m, 2H), 1.75 (m, 7H), 1.24 (m, 1H). MS (m/z): 452 [MH]$^+$.

General Procedures to Examples 4-5

Table 1

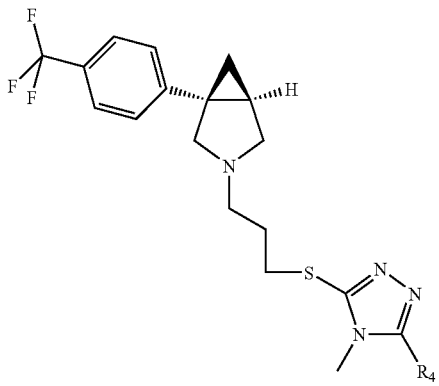

To a solution of the respective 3-thio-5-$R_4$-1,2,4-triazole (0.082 mmol) in dry acetonitrile (2 ml) 2-tert-butylimino-2-diethylamino-1,3-dimethyl-perhydro-1,3,2-diaza-phosphorine on polystyrene (56 mg, 2.2 mmol/g) was added and the resulting mixture was shaken for 30 minutes at room temperature then (1S,5R)-3-(3-chloropropyl)-1-[4-(trifluoromethyl)phenyl]-3-azabicyclo[3.1.0]hexane (25 mg) was added and the resulting mixture was shaken at 50° C. overnight. After cooling the resin was filtered off, washed with methanol (2 ml) and then the solvent was removed under reduced pressure. Purifications were carried out using mass directed HPLC using a Waters XTerra Prep MS C18 10 μm, 100×19 mm column using the following conditions Mobile phase: A: NH4HCO3 sol. 10 mM, pH10; B: CH3CN Gradient 1: 30% (B) for 1 min, from 30% (B) to 95% (B) in 9 min, 95% (B) for 3 min Flow Rate: 17 ml/min UV Wavelength Range: 210-350 nm Mass Range: 100-900 amu Ionization: ES+

Then solvent was removed under reduced pressure to give title compounds as a free bases.

HPLC:

Analytical

Column: X Terra MS C18 5 μm, 50×4.6 mm

Mobile Phase: A: NH4HCO3 sol. 10 mM, pH10; B: CH3CN

Gradient: 30% (B) for 1 min, from 30% (B) to 95% (B) in 9 min, 95% (B) for 3 min Flow rate: 1 ml/min UV wavelength range: 210-350 nm Mass range: 100-900 amu Ionization: ES+

The thiotriazoles used in the preparation of Examples 4-5 are commercially available.

All publications, including but not limited to patents and patent applications, cited in this specification are herein incorporated by reference as if each individual publication were specifically and individually indicated to be incorporated by reference herein as though fully set forth.

It is to be understood that the present invention covers all combinations of particular groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A compound of formula (I) or a pharmaceutically acceptable salt thereof:

wherein
- G is selected from the group consisting of: phenyl, pyridyl, benzothiazolyl, and indazolyl;
- p is an integer ranging from 0 to 5;
- $R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl, $SF_5$; and $R_5$;
- $R_2$ is hydrogen or $C_{1-4}$alkyl;
- $R_3$ is $C_{1-4}$alkyl;
- $R_4$ is $C_{1-4}$ alkyl or $C_{1-6}$ cycloalkyl optionally substituted by 1 or 2 substituents selected from the group consisting of: halogen, cyano, $C_{1-4}$alkyl, halo$C_{1-4}$alkyl, $C_{1-4}$alkoxy, and $C_{1-4}$alkanoyl;
- $R_5$ is selected from the group consisting of: isoxazolyl, —$CH_2$—N-pyrrolyl, 1,1-dioxido-2-isothiazolidinyl, thienyl, thiazolyl, pyridyl, 2-pyrrolidinonyl, and each

TABLE 1

| Ex. N. | Structure | Compound Name | Retention time (min) | MS (m/z) [MH]+ |
|---|---|---|---|---|
| 4 | 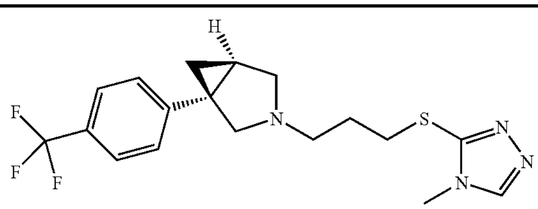 | (1S,5R)-3-{3-[(4-methyl-4H-1,2,4-triazol-3-yl)thio]propyl}-1-[4-(trifluoromethyl)phenyl]-3-azabicyclo[3.1.0]hexane | 7.44 | 383 |
| 5 | | (1S,5R)-3-{3-[(4,5-dimethyl-4H-1,2,4-triazol-3-yl)thio]propyl}-1-[4-(trifluoromethyl)phenyl]-3-azabicyclo[3.1.0]hexane | 6.27 | 397 | group is optionally substituted by one or two substituents selected from the group consisting of: halogen, cyano, $C_{1-4}$alkyl, halo$C_{1-4}$alkyl, $C_{1-4}$alkoxy, and $C_{1-4}$alkanoyl.

2. A compound as claimed in claim 1, having a formula (IA) or a salt thereof:

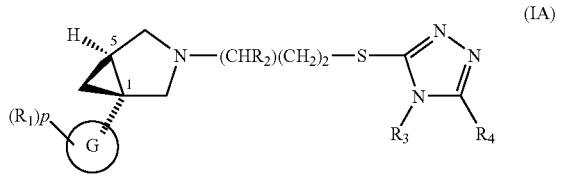

wherein G, p, $R_1$, $R_2$, $R_3$, $R_4$, and $R_5$ are defined in claim 1.

3. A compound as claimed in claim 1, having a formula (IB') or a salt thereof:

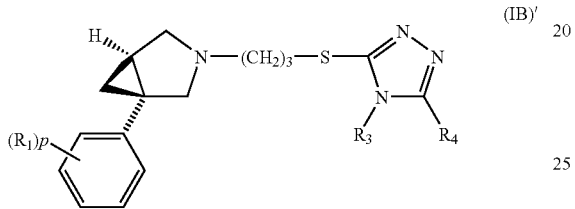

wherein p, $R_1$, $R_3$, $R_4$, are defined in claim 1.

4. A compound as claimed in claim 1, which is
(1S,5R)-3-{3-[(5-cyclopropyl-4-methyl-4H-1,2,4-triazol-3-yl)thio]propyl}-1-[4-(trifluoromethyl)phenyl]-3-azabicyclo[3.1.0]hexane;

(1S,5R)-3-(3-{[5-(1,1-dimethylethyl)-4-methyl-4H-1,2,4-triazol-3-yl]thio}propyl)-1-[4-(trifluoromethyl)phenyl]-3-azabicyclo[3.1.0]hexane;

(1S,5R)-3-{3-[(5-cyclopentyl-4-methyl-4H-1,2,4-triazol-3-yl)thio]propyl}-1-[4 (trifluoromethyl)phenyl]-3-azabicyclo[3.1.0]hexane;

(1S,5R)-3-{3-[(4,5-dimethyl-4H-1,2,4-triazol-3-yl)thio]propyl}-1-[4-(trifluoromethyl)phenyl]-3-azabicyclo[3.1.0]hexane;

(1S,5R)-3-{3-[(4-methyl-4H-1,2,4-triazol-3-yl)thio]propyl}-1-[4-(trifluoromethyl)phenyl]-3-azabicyclo[3.1.0]hexane;

or a salt thereof.

5. A pharmaceutical composition comprising a compound as claimed in claim 1 or a pharmaceutically acceptable salt thereof and a pharmaceutically acceptable carrier.

* * * * *